United States Patent
Unsworth et al.

(10) Patent No.: US 7,580,801 B2
(45) Date of Patent: Aug. 25, 2009

(54) MONITORING OF TWO-PHASED FLUID FLOW

(75) Inventors: Peter Joseph Unsworth, Lewes (GB); Edward Hall Higham, Redhill (GB); Mongkol Pusayatanont, Sussex (GB)

(73) Assignee: University of Sussex Intellectual Property Limited, Brighton (GB)

( * ) Notice: Subject to any disclaimer, the term of this patent is extended or adjusted under 35 U.S.C. 154(b) by 103 days.

(21) Appl. No.: 10/516,567

(22) PCT Filed: May 30, 2003

(86) PCT No.: PCT/GB03/02376

§ 371 (c)(1),
(2), (4) Date: Apr. 3, 2006

(87) PCT Pub. No.: WO03/102511

PCT Pub. Date: Dec. 11, 2003

(65) Prior Publication Data

US 2006/0217899 A1    Sep. 28, 2006

(30) Foreign Application Priority Data

May 31, 2002   (GB)   ................................. 0212739.7

(51) Int. Cl.
*G01F 1/32* (2006.01)
(52) U.S. Cl. .............................. 702/50; 702/45; 702/48; 702/106; 73/861.22; 73/861.24
(58) Field of Classification Search .................. 702/50, 702/45, 48, 106; 73/861.22, 861.24, 861.355, 73/861.357
See application file for complete search history.

(56) References Cited

U.S. PATENT DOCUMENTS

| | | | | |
|---|---|---|---|---|
| 3,885,432 A | * | 5/1975 | Herzl | 73/861.22 |
| 3,982,434 A | * | 9/1976 | McMurtrie | 73/861.22 |
| 4,015,472 A | * | 4/1977 | Herzl | 73/861.22 |
| 4,083,241 A | * | 4/1978 | Herzl | 73/861.24 |
| 4,094,194 A | * | 6/1978 | Herzl | 73/861.24 |
| 4,134,297 A | * | 1/1979 | Herzl | 73/861.24 |
| 4,876,897 A | * | 10/1989 | DeCarlo et al. | 73/861.04 |
| 4,973,062 A | | 11/1990 | Lew | |
| 5,095,760 A | * | 3/1992 | Lew | 73/861.24 |
| 5,121,658 A | * | 6/1992 | Lew | 73/195 |
| 5,463,904 A | * | 11/1995 | Kalinoski | 73/861.24 |
| 5,796,010 A | * | 8/1998 | Kishiro et al. | 73/861.357 |
| 6,170,338 B1 | * | 1/2001 | Kleven et al. | 73/861.22 |
| 6,298,734 B1 | * | 10/2001 | Storer et al. | 73/861.22 |

(Continued)

FOREIGN PATENT DOCUMENTS

EP    0077764 A1    4/1983

OTHER PUBLICATIONS

Great Britain Search Report for Application No. GB 0212739.7, dated Nov. 11, 2002.

(Continued)

*Primary Examiner*—Carol S Tsai
(74) *Attorney, Agent, or Firm*—Lahive & Cockfield, LLP

(57) ABSTRACT

In a method of monitoring two-phase fluid flow a vortex flowmeter is used to generate a signal indicative of the flow regime using the signal components and its fluctuations to determine the phase status of the fluid flow.

21 Claims, 11 Drawing Sheets

U.S. PATENT DOCUMENTS

| | | | | |
|---|---|---|---|---|
| 6,412,352 | B1 * | 7/2002 | Evans et al. | 73/861.04 |
| 6,412,353 | B1 * | 7/2002 | Kleven et al. | 73/861.22 |
| 6,484,590 | B1 * | 11/2002 | Kleven et al. | 73/861.22 |
| 6,557,422 | B1 * | 5/2003 | Kolahi | 73/861.357 |
| 6,651,512 | B1 * | 11/2003 | Kleven et al. | 73/861.22 |
| 6,658,945 | B1 * | 12/2003 | Kleven | 73/861.22 |
| 6,810,719 | B2 * | 11/2004 | Dutton et al. | 73/61.44 |
| 6,993,445 | B2 * | 1/2006 | Clarke et al. | 702/106 |
| 7,013,715 | B2 * | 3/2006 | Dutton et al. | 73/61.44 |
| 2005/0229716 | A1 * | 10/2005 | Unsworth et al. | 73/861.53 |

OTHER PUBLICATIONS

Great Britain Search Report for Application No. GB0428398.2, dated Feb. 4, 2005.

Foussat, A., et al. "Vertical Liquid-Liquid and Liquid-Gas Two-Phase Flow Measurements with a Vortex Flow Meter." *Measuring Techniques in Gas-Liquid Two-Phase Flows, Symposium*, 1984, pp. 651-676.

Khan, H., et al. "Statistical Characterization of Air Water Bubbly Flow Using Differential Pressure Drop Measurements." *Proceedings of the Fluids Engineering Conference*, Jun. 20-24, 1993, pp. 137-149.

Mi, Y. et al. "Flow Regime Identification Methodology with Neural Networks and Two-Phase Flow Models." *Nuclear Engineering and Design*, Feb. 2001, 204(1-3):87-100.

Pusayatanont, M., et al. "Two-Phase Flow Measurement Based on the Analysis of the Sensor Signal from a Conventional Vortex Flowmeter." *Proceedings 11th International Conference on Flow Measurement (Flomeko, 2003)*, May 12-14, 2003, Paper 128, pp. 1-8.

* cited by examiner

O — training target
* — Neural output after training
x — Neural output after testing

MONITORING OF TWO-PHASED FLUID FLOW

This invention concerns improvements in or relating to the monitoring of two-phase fluid flow and more particularly concerns the detection and measurement of fluid flow.

In particular the present invention has reference to the detection of the presence of a second phase component in fluid flow, and to the determination of the relative magnitude of each phase in a two-phase gas/liquid flow regime by analysis of the unconditioned sensor signal from a conventional single-phase flowmeter.

There are many different types of flowmeter including the orifice plate/DP flowmeter, the turbine flowmeter, the Coriolis flowmeter, the electromagnetic flowmeter, and the vortex flowmeter, each employing different operational mechanisms and methods of detecting the flow being measured to yield a metered reading. The selection of the flowmeter type will depend inter alia upon the specific application, its cost, reliability and accuracy. Each type has its attendant disadvantages and advantages.

The present invention has particular, although not exclusive reference to vortex flowmeters in which Von Karman vortices are generated by the presence of a bluff body, for example a shedder bar, placed perpendicular to the direction of flow across and centrally within the confining conduit in which the fluid flows.

Consider in FIG. 15 of the accompanying drawings a cylindrical bluff body diameter D immersed in a flowing fluid. If the Reynolds Number is less than about 0.5, the two boundary layers around the cylinder do not detach because the pressure gradients (which depend on $v^2$) are very small.

For Reynolds Numbers between about 2 and 30 the flow boundary layers separate symmetrically producing two mirror image vortices before the flow recombines. As the Reynolds Number is increased the vortices start to shed alternately from each side of the cylinder producing two staggered rows of vortices. This is the Karman Vortex Street. Each vortex is in the field of every other vortex so if such a system of vortices could exist in a stationary fluid the system would move upstream.

Under real conditions the frequency of vortex shedding is determined by the Strouhal Number, St, which for a cylindrical bluff body is fD/U given by 0.198 (1-19.7/Re), where f is the vortex shedding frequency, D is the diameter of the cylinder, U is the mean flow velocity, and Re is the Reynolds number.

Hence $$Q = k_1 \times f$$

where Q is the volumetric flow rate and $k_1$ is a constant

The frequency of the vortex shedding is essentially a function of the velocity of the flowing fluid and is largely independent of its physical properties inter alia temperature, pressure, density, viscosity, conductivity, etc., provided that the presence of vortices can be sensed reliably and practically and this typically depends on the Reynolds Number being greater than about 10,000.

In the operation of vortex flowmeters, methods used to detect the shedding of the vortices involve sensing changes in the fluid pressure adjacent to the vortex shedding body caused by the transit of the vortices using either a differential pressure sensor, or sensing the force exerted by the moving vortices on a fixed vane, or sensing the torque exerted by the vortices on the vortex shedding body, or observing the effect of the vortices on a transverse ultrasonic beam.

A unique feature of the vortex flowmeter is that the effect of the vortex shedding body on the fluid flow is essentially the same as that caused by any obstruction or change in the cross section of the conduit in which the fluid is flowing and is in accordance with Bernoulli's equation:

$$P/\rho g + v^2/2g + z = \text{constant}$$

where P is the pressure, $\rho$ is the density, v is the fluid velocity, and g is the gravitational acceleration.

Hence the pressure drop across the vortex shedding body is a function of the square of the flow velocity as well as the density of the flowing fluid and $$Q = k_2 \times (\Delta P/\rho)^{1/2}$$

where Q is the volumetric flow rate $\Delta P$ is the differential pressure developed across the vortex shedding body and $k_2$ is a further constant In a steady flow rate regime and when a differential pressure sensor is used to detect the vortices, the oscillating signal from the vortex sensor is characterised by variations in periodicity of as much as ±10% and even wider fluctuations in amplitude. It is customary, therefore, to condition the sensor signal so that these fluctuations are eliminated. For a typical vortex flowmeter operating in a single-phase fluid, the frequency of the vortex shedding is proportional to the volumetric flow rate Q and the average amplitude ($A_0$) of the vortex sensor signal increases as the square of the volumetric flow rate:

That is $$A_0 = a Q^2$$

where $$\alpha = \frac{\rho \gamma G_A C_p}{a}$$

and $\rho$ = the fluid density (kg/m³)

$G_A$ = the gain of the amplifier $\gamma$ = the sensor sensitivity (VN$^{-1}$ m²)

a = the area of the pipe line (m²)

$C_p$ = the pressure coefficient which is constant for the same line size of flowmeter In order to determine the power and rms amplitude of the vortex sensor signal, the power is calculated by summing the sample signals x(n) according to the equation:

$$\text{Signal power} = \frac{\sum_{n=1}^{N} x^2(n)}{N}$$

where N is the number of sampled data points, and the rms signal amplitude can be calculated from the square root of the signal power.

In some industries, notably for example the petrochemical industry, the flowing fluid may not be a single component. For example, it may be a hydrocarbon liquid in which there is entrained a significant proportion of hydrocarbon gas, or it may be the reverse where the principal component is a hydrocarbon gas which is carrying a significant proportion of hydrocarbon liquid in the form of droplets.

Alternatively, it may be a single component fluid (e.g. ethylene or ammonia) which is flowing under conditions of pressure and temperature where it can exist as either a liquid or gas. In all these cases, it is a requirement to establish during operation of the relevant process or activity, not only the volumetric or mass flow rate but also the relative magnitudes of the individual phases. In other fields for example in steam generation, steam quality in terms of its wetness is an important characteristic influencing the operational efficiency of the relevant plant.

Conventionally, as indicated above, the amplitude and periodicity fluctuations in the signal from the sensor are deliberately suppressed in order to give a purer signal. However, we have found that analysis of such fluctuations can yield valuable information regarding the fluid flow regime.

It is therefore an object of the present invention to provide a method of monitoring two-phase fluid flow by analysing the said signal and fluctuations.

Another object of the present invention is to provide a method of detecting the presence of a second fluid phase.

A still further object of the present invention is to provide a method of metering two-phase fluid flow to yield either the volumetric flow rate of each component of a two component fluid or the relative magnitudes of the phases in a single component two-phase flow.

According to a first aspect of the invention there is provided a method of monitoring fluid flow in a closed conduit including the disposition of a flowmeter through which the fluid to be monitored flows, generating a signal indicative of at least one characteristic of the fluid flow, measuring the signal components and retaining the fluctuations associated therewith, and analysing the said signal components and fluctuations to determine the at least one characteristic of the fluid flow.

According to a second aspect of the invention there is provided a method of detecting two-phase fluid flow in a fluid flow in a closed conduit including the disposition of a flowmeter through which the fluid to be detected flows, generating a signal indicative of at least one characteristic of the fluid flow, measuring the signal components and retaining the fluctuations associated therewith, and analysing the said signal components and the fluctuations to detect the presence or absence of two-phase fluid flow.

According to a third aspect of the present invention there is provided a method of metering fluid flow in a closed conduit including the disposition of a fluid flowmeter through which the fluid to be metered flows, generating a signal indicative of at least one characteristic of the fluid flow, measuring the signal components and retaining the fluctuations associated therewith, and analysing the said signal components and fluctuations to determine the volumetric flow rate of at least one phase of the fluid flow. Conveniently the flowmeter is a vortex flowmeter in which the means of sensing the signal generated by the flowmeter may be of the differential pressure type. It is to be understood that the use of a flowmeter other than a vortex flowmeter is within the scope of the invention.

We have found that the presence of a second fluid phase has a direct effect on the oscillating signal from the vortex sensor. In additional to changing the shedding frequency, which causes measurement error if the second phase is unexpected, the amplitude of the vortex oscillation and the associated fluctuations can change to a far greater degree than would be expected from the change in the overall density due to mixing heavy and light fluids, or from the increase in velocity. At any particular shedding frequency produced by two-phase flow, the change in the signal amplitude and the strength of the signal fluctuations depend on the amount of second phase present, and can enable detection of the presence of the second phase, and allow metering of the flow rates of both phases simultaneously.

The method of the invention also, includes the steps of calibrating the flowmeter by the use of reference flowmeters to accurately establish the flow rates of the individual components before they are mixed to form the two-phase flow to be measured by the flowmeter, in order to determine a relationship between signal power, signal amplitude (rms), the shedding frequency in relation to a vortex flowmeter, the signal fluctuations, and the flow rate. For two-phase flow measurement, the calibration of the flowmeter involves the conduct of a test programmed to give performance data over a range of flow rates with single and two-phase flow. In particular two-phase flow was selected by the inventors in terms of providing one distinct primary phase and a distinct secondary phase; for example water was the primary phase with the secondary phase being air. Essentially therefore the calibration was carried out on the basis of gas-in-liquid phases, but it will be appreciated that the calibration could be carried out with the phases in reverse.

The calibration yields graphical data on the measured signal features providing volumetric flow measurements enabling the use of the flowmeter to determine the presence of single or two-phase flow, and to measure the volumetric flow in single component flow, or the volumetric flows of both components in two-phase flow.

It has been found that the presence of a secondary phase within a primary phase occasions a change in the features of the flow measurement signal. Thus for example in the case of air being introduced into water flowing at a constant rate, this produces changes in the measured signal features. The vortex shedding frequency, which is an indicator as to the mean velocity of flow, increases with a decrease in the amplitude and power of the sensor signal, and it is this decrease which hitherto has been regarded as redundant that provides the important information regarding to the phase fractions in the two-phase flow.

The relative magnitude of the two phases in a gas-in-liquid and liquid-in-gas flow regimes can be determined by analysis and manipulation of the unconditioned sensor signal from a vortex flowmeter in particular.

It is envisaged that the method of the present invention may be applied to flow regimes other than that indicated above, and accordingly could be applicable to liquid-in-liquid flow regimes where the liquids are immiscible, liquids or gases with entrained solids, and three-phase flow regimes.

By way of example only there follows a description of the utilisation of a vortex flowmeter to generate a signal indicative of the volumetric flow rate of two components of two-phase gas-in-liquid fluid flows with reference to the accompanying figures in which.

Figure 1:
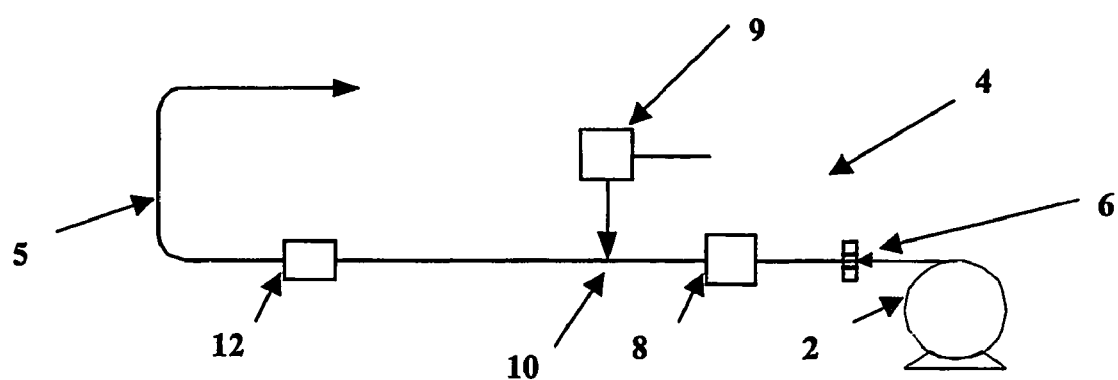
FIG. 1 is a schematic diagram of the apparatus to generate two-phase air-in-water flow.

FIG. 1 shows a schematic diagram of laboratory test apparatus for the generation of two-phase air-in water flow and consists of a pump 2 for delivering water to a flow loop 4 comprising pipework 5. The pump 2 delivers water into the pipework of the circuit through a flow conditioner 6 that smoothes the flow and thence through a first reference flowmeter 8. Downstream of the flowmeter 8 is located an air injection point 10 through which air may be injected into the water flow through a second reference meter 9.

A vortex flowmeter 12 is disposed in the circuit 4 downstream of the air injection point 10, the pipework 5 continuing further and ultimately discharging into a reservoir for recycling.

Figure 2:
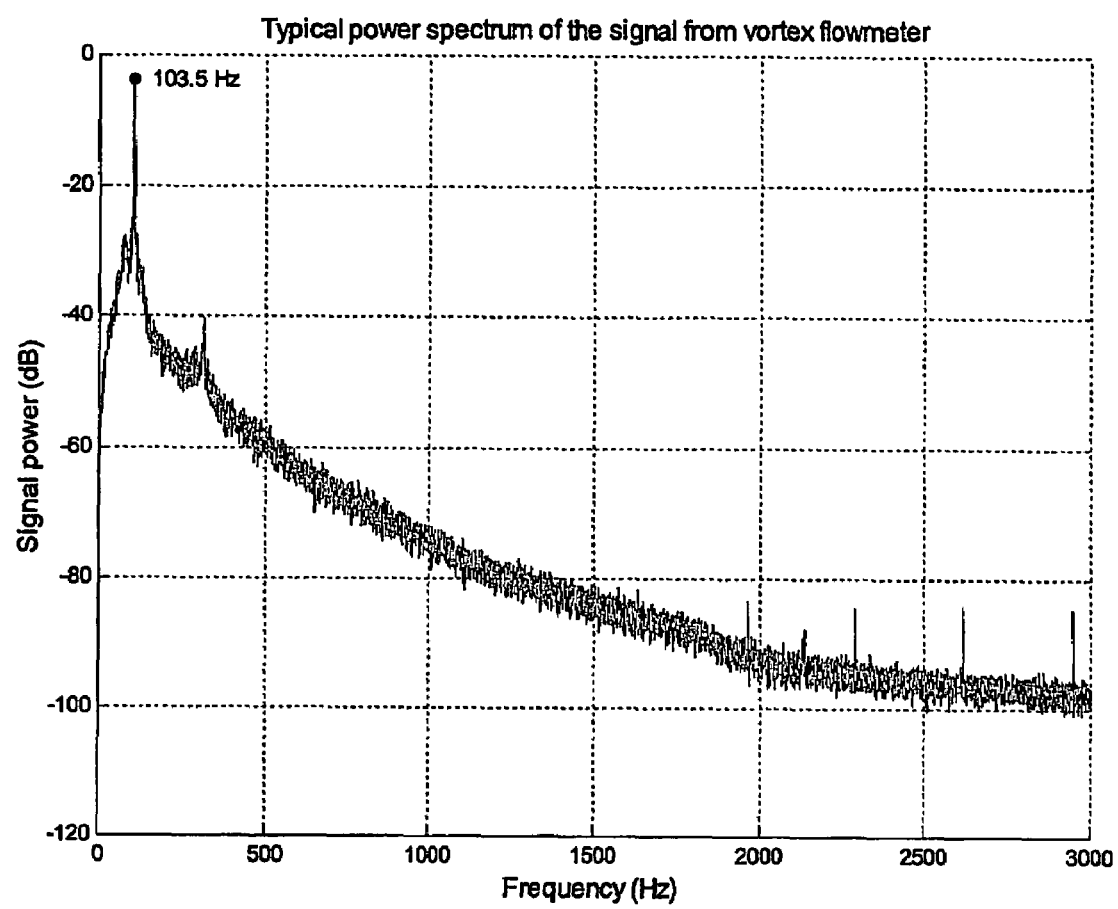
FIG. 2 shows a typical power spectrum of the sensor signal from a vortex flowmeter, with the peak at the vortex shedding frequency.
Figure 3:
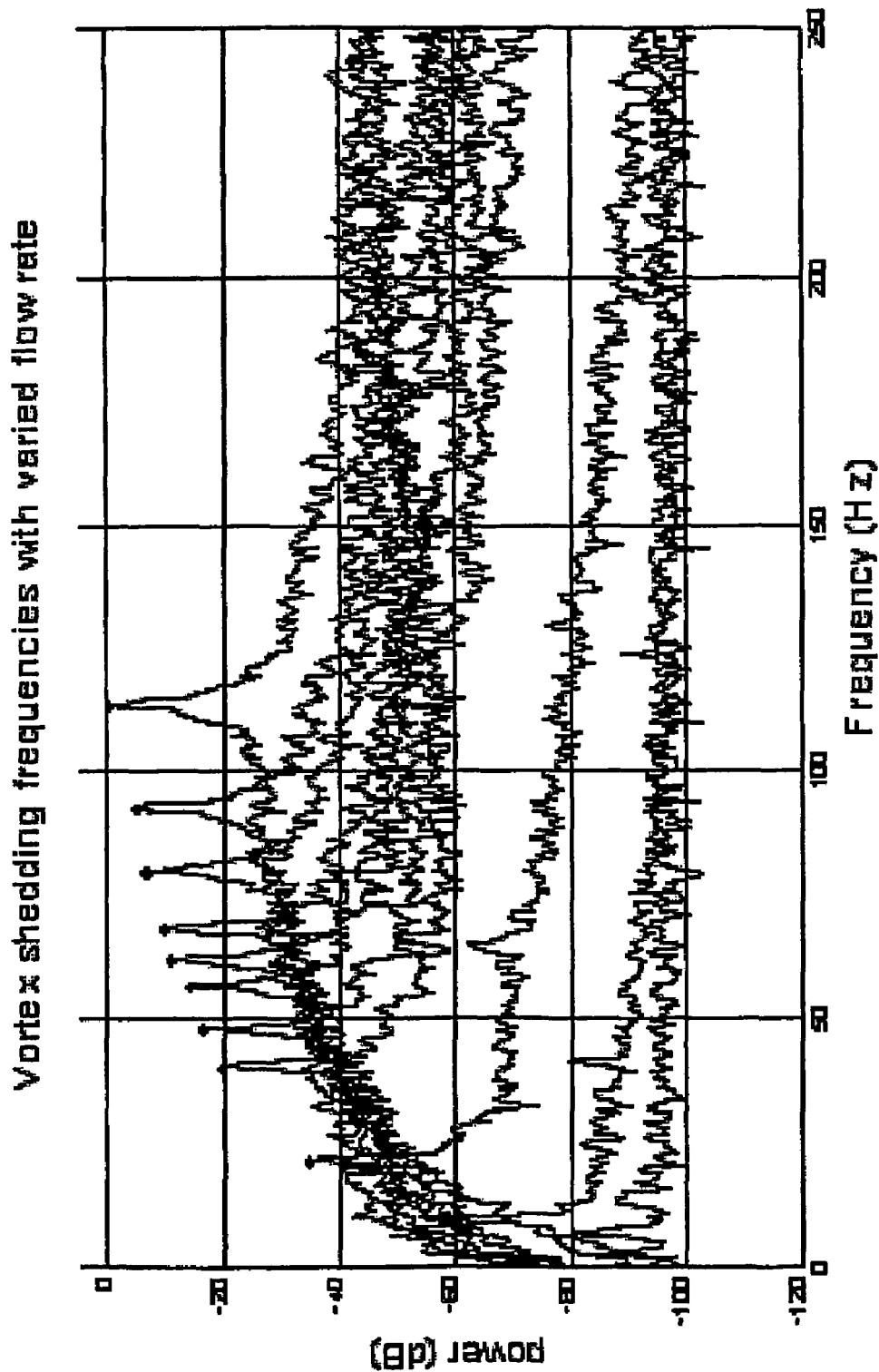
FIG. 3 shows the variation of the power spectrum with liquid flow rate for a vortex flowmeter with single-phase flow.
Figure 15:
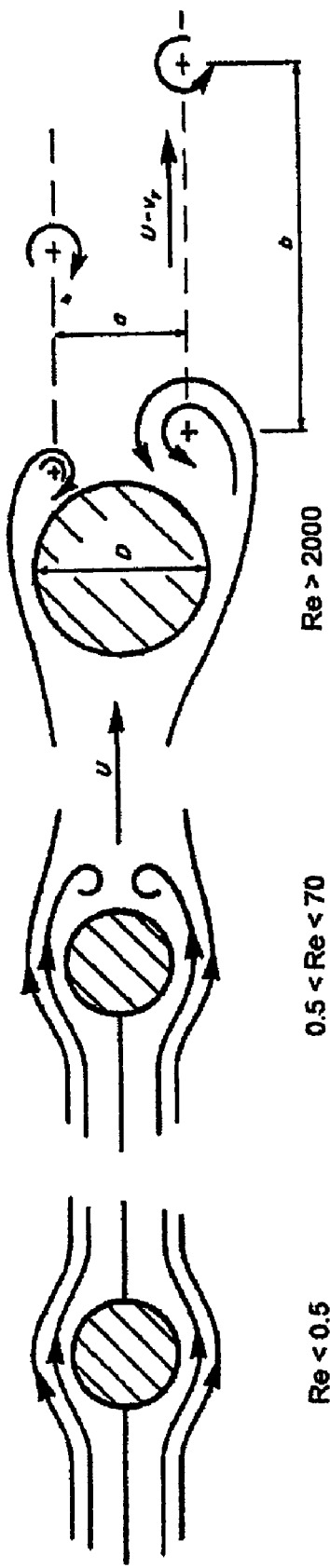
FIG. 15 is a diagram representing a cylindrical bluff body and illustrating vortices generated during fluid flow at flow rates represented by three groups of values of Reynolds number.

As has hereinbefore been explained vortex flowmeters depend for their operation on the alternate shedding of vortices from the two edges of a bluff body positioned perpendicular to the direction of flow in the stream of fluid (see FIG. 15). The frequency of the vortex shedding is proportional to the velocity of flow and the frequency spectrum of the unconditioned sensor signal from a typical vortex flowmeter is shown in FIG. 2. The frequency peak is at the vortex shedding frequency.

Figure 7:
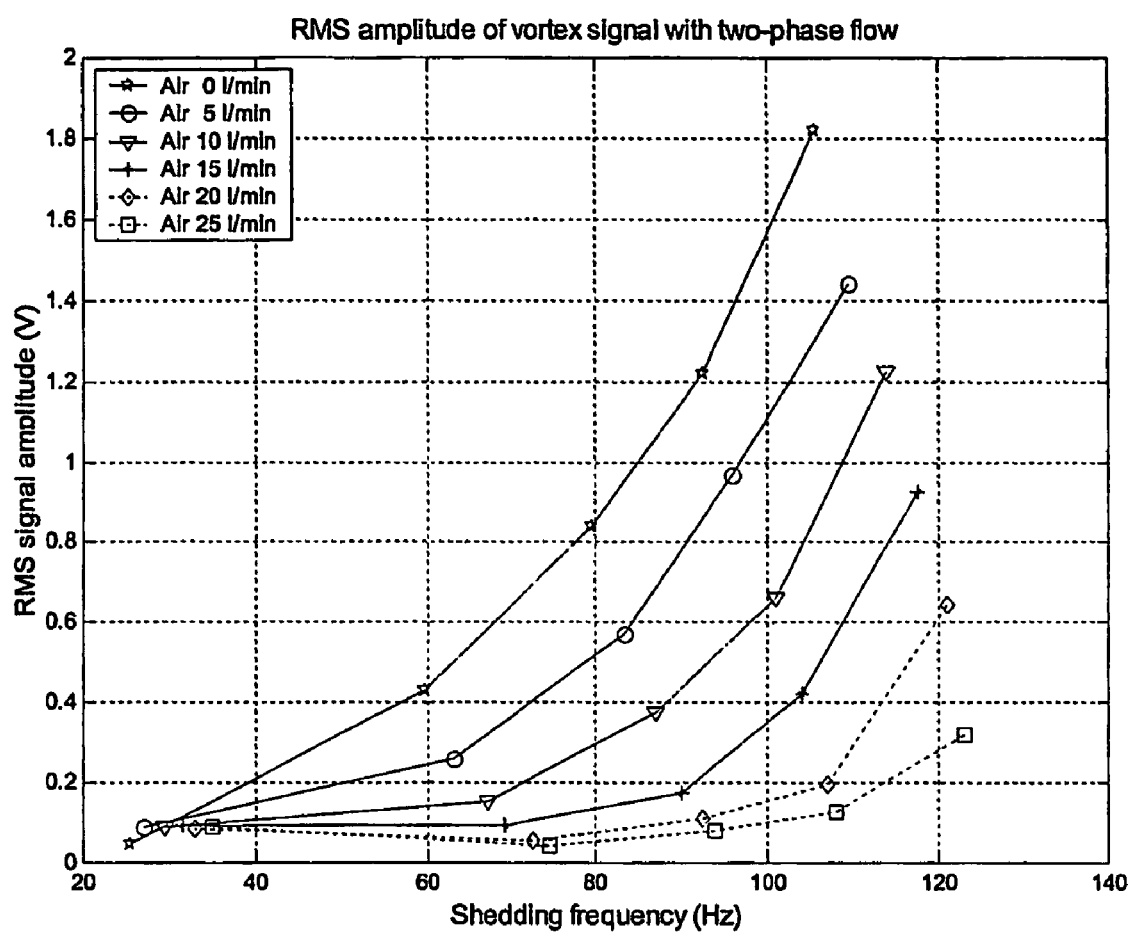
FIG. 7 shows a change in the rms amplitude of the vortex sensor signal with the primary phase (water) flow rate for different flow rates of a secondary phase (air).
Figure 12:
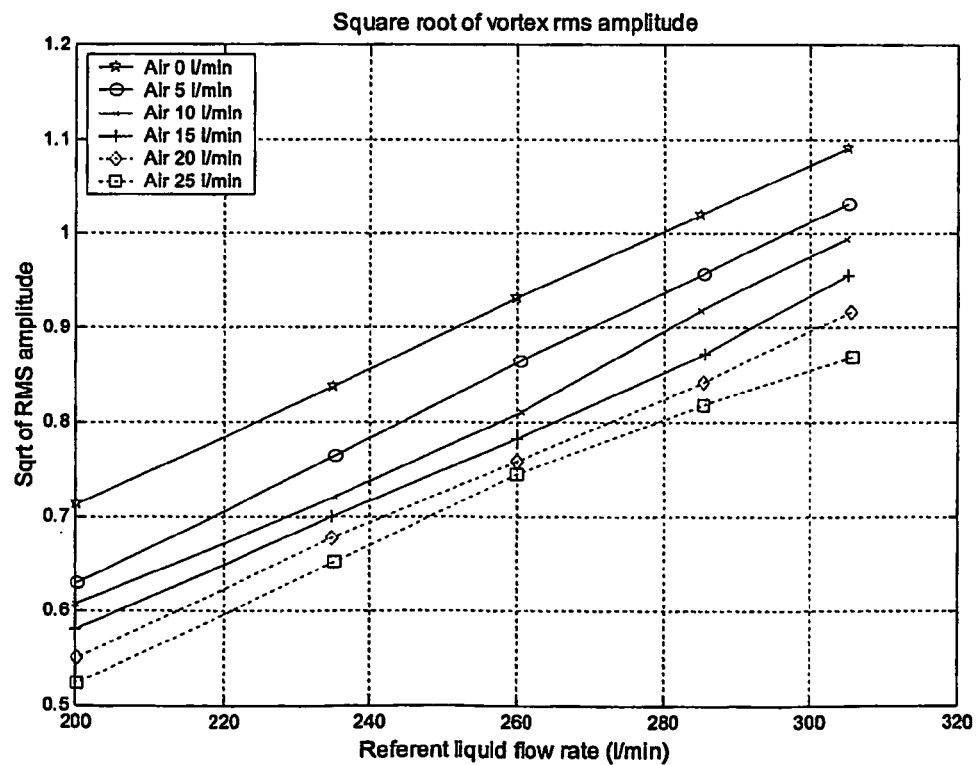
FIG. 12 shows a plot of the square root of the vortex signal amplitude against liquid flow rate for different injected air flow rates.

When the flowmeter 12 is operating on a single-phase liquid, the amplitude of the signal increases according to the square of the vortex shedding frequency, as shown in FIG. 7 (top plot) and FIG. 12 (top plot). This relationship is a direct function of the pressure drop developed across the vortex shedding bar and confirms that Bernoulli's equation (shown supra) applies to the operation of the flowmeter.

Figure 4:
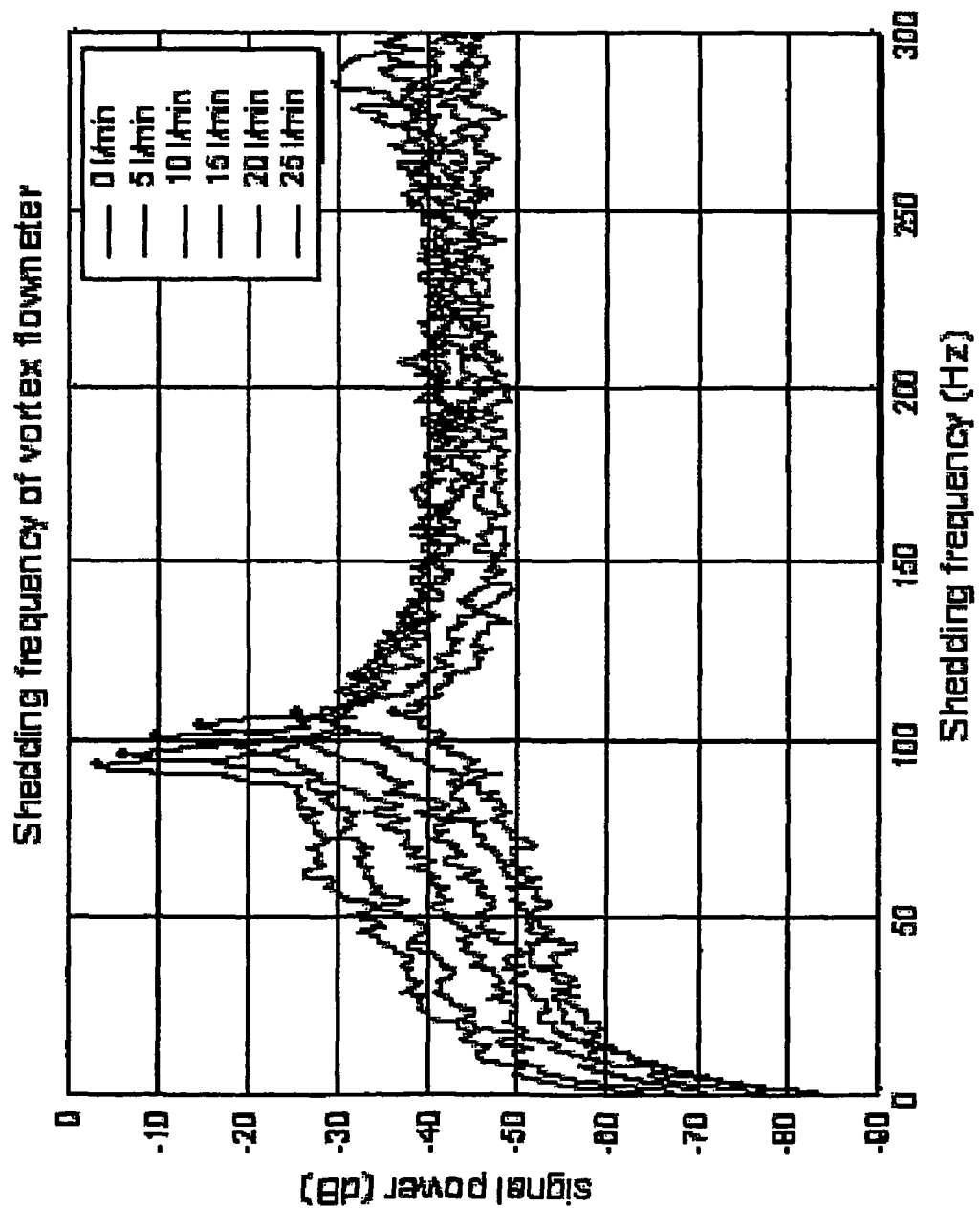
FIG. 4 shows the change in the amplitude and frequency of the vortex sensor signal resulting from the introduction of a secondary phase (air).

If the flow of the primary phase (water) is held constant, the introduction of a secondary phase (air for example) through point 10 causes the shedding frequency to rise, because of the increased total volume of the flowing fluid. However it also causes the amplitude of the vortex sensor signal to fall, as shown in FIG. 4, but much more rapidly with increasing air fraction than could be explained if the mean density of the two-phase mixture is inserted for the density $\rho$ in the Bernoulli equation.

Figure 5:
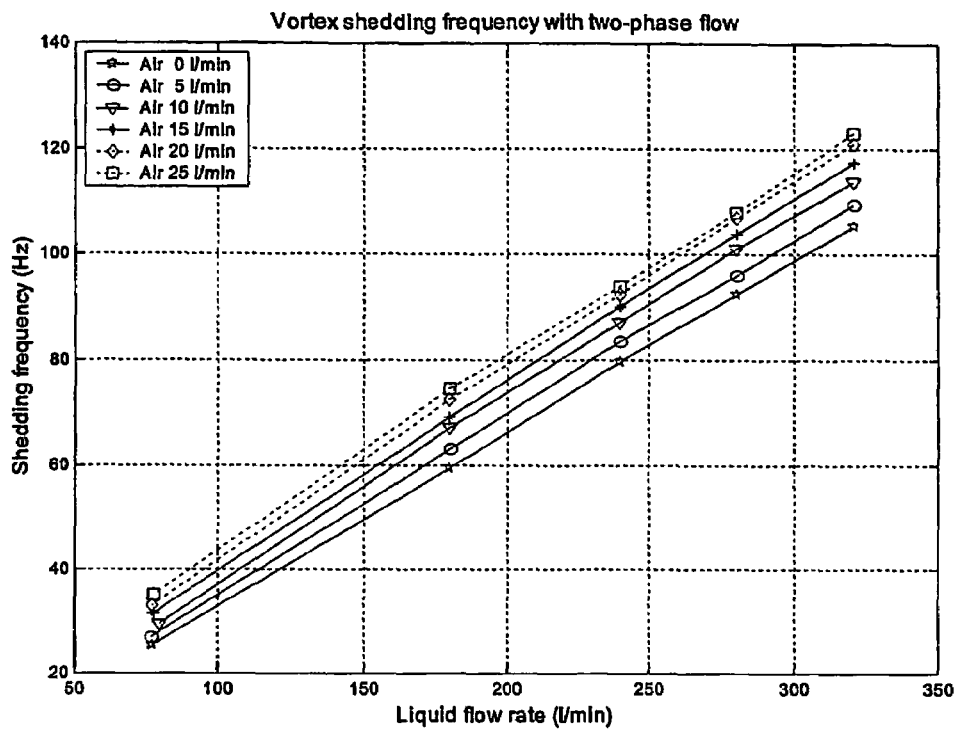
FIG. 5 shows a change in the vortex shedding frequency with flow rate of the primary phase (water) resulting from the introduction of a secondary phase (air).

If the flow rate of the primary phase (water) is held constant at a particular flow rate, the introduction of a secondary phase (air) causes the frequency of the vortex shedding to rise. This result is shown in FIG. 5 for five fixed primary phase flow rates. Each line is plotted at a fixed value of the injected air flow rate. The bottom line is for single-phase water flow.

Figure 6:
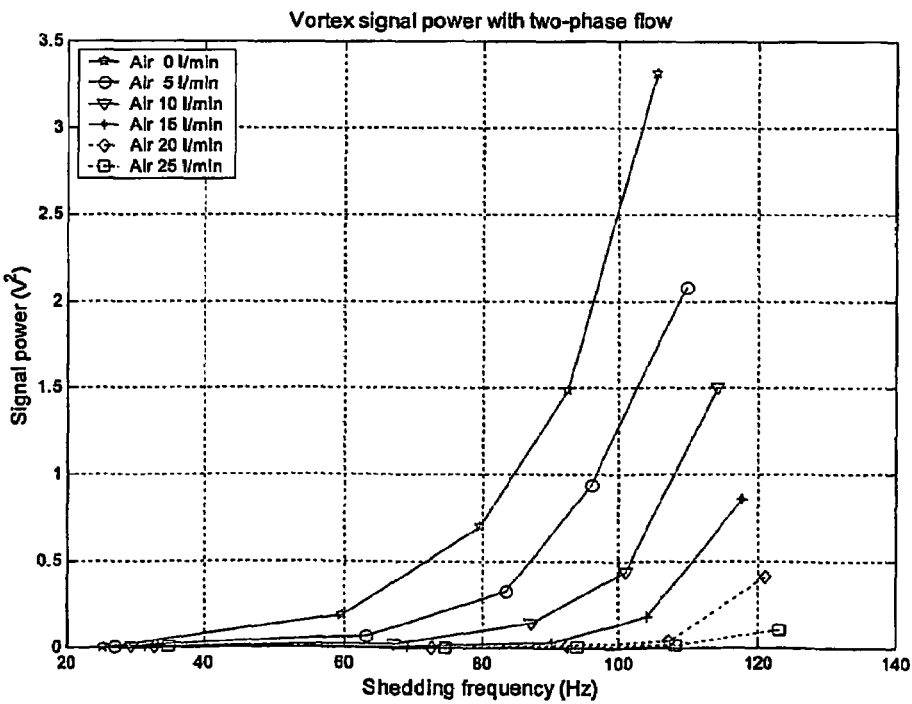
FIG. 6 represents a change in the power of the vortex sensor signal with flow rate of the primary phase (water) and the introduction of a secondary phase (air).

When operating on a single-phase flow, the relative amplitude of the sensor signal is directly proportional to the square of the shedding frequency, as show in FIG. 6. If a secondary phase (air) is introduced, the relative amplitude of the signal falls away progressively. It is therefore possible to plot a series of curves which correlate the vortex shedding frequency with the volumetric flow rate and hence the relative magnitude of the two phases.

The power and the amplitude of the vortex sensor signal over a range of two-phase flows are shown in FIGS. 6 and 7 respectively. Each curve shows the signal as the primary phase (water) flow rate is varied for a fixed secondary phase (air) flow rate.

To determine the relative magnitudes of the individual flows in a two-phase regime, the flowmeter 12 must first be calibrated involving the measurement and plotting of the amplitude and shedding frequency of the sensor signal over the range of single-phase flows of the primary fluid to be covered by the flowmeter. The procedure must then be repeated with the flow rate of the primary fluid held constant, but with the flow rate of the secondary fluid varied throughout the range to be covered. FIGS. 5, 6, and 7 are examples of such calibrations.

In this context FIGS. 5, 6, and 7 show the results of measurements made at line pressures up to 3 bar on a (1½ inch) Foxboro Model 83F Vortex Flowmeter. For FIG. 5 the frequency of vortex shedding was measured with the flow rate of the primary phase (water) held constant at five different values and while the flow rate of the secondary phase (air) was adjusted from zero to the maximum in five equal steps. For FIG. 6 the signal power and vortex shedding frequency were measured with the flow rate of the primary phase held constant at five different values and the flow rate of the secondary phase was adjusted from zero to the maximum in five equal steps. For FIG. 7 the signal amplitude and vortex shedding frequency were measured with the flow rate of the primary phase held constant at five different values and the flow rate of the secondary phase was adjusted from zero to the maximum in five equal steps. On the basis of these plots the flow rates of the two phases can be determined for any set of conditions within the calibrated range. Thus if the vortex shedding frequency is for example 100 Hz and the signal amplitude is about 0.64 V, then the data in FIG. 7 show that the flow rate of the primary fluid is about 280 l/min and that of the secondary phase is about 10 l/min.

It is evident that a series of curves which correlate the vortex shedding frequency with the mass flow rate can be prepared for other line sizes of vortex flowmeters and from them the relative magnitude of the two-phases can be deduced.

It is clear that the magnitude and the power of vortex sensor signal discriminate between the measurement signals when different amounts of secondary phase are introduced into the primary phase. FIGS. 6 and 7 show the systematic but non-linear relationships exhibited between the observable quantities (shedding frequency, amplitude and power of vortex sensor signal) and the flow rates of individual phases, namely the primary phase (water) flow rate and the secondary phase (air) flow rate, which the flowmeter should ideally measure. A multi-layer neural network is capable of fitting complex non-linear data, and therefore provides a method for handling the observable data to produce a system which can yield good measured values for both the primary and the secondary phase flow rates.

Four input data values from the vortex flowmeter are used as inputs to the neural network and they are the shedding frequency, signal power, rms signal amplitude, and the square root of rms signal amplitude. The network is trained to generate two output values, the primary phase (water) flow rate and the secondary phase (air) flow rate from the four input values.

Figure 8:
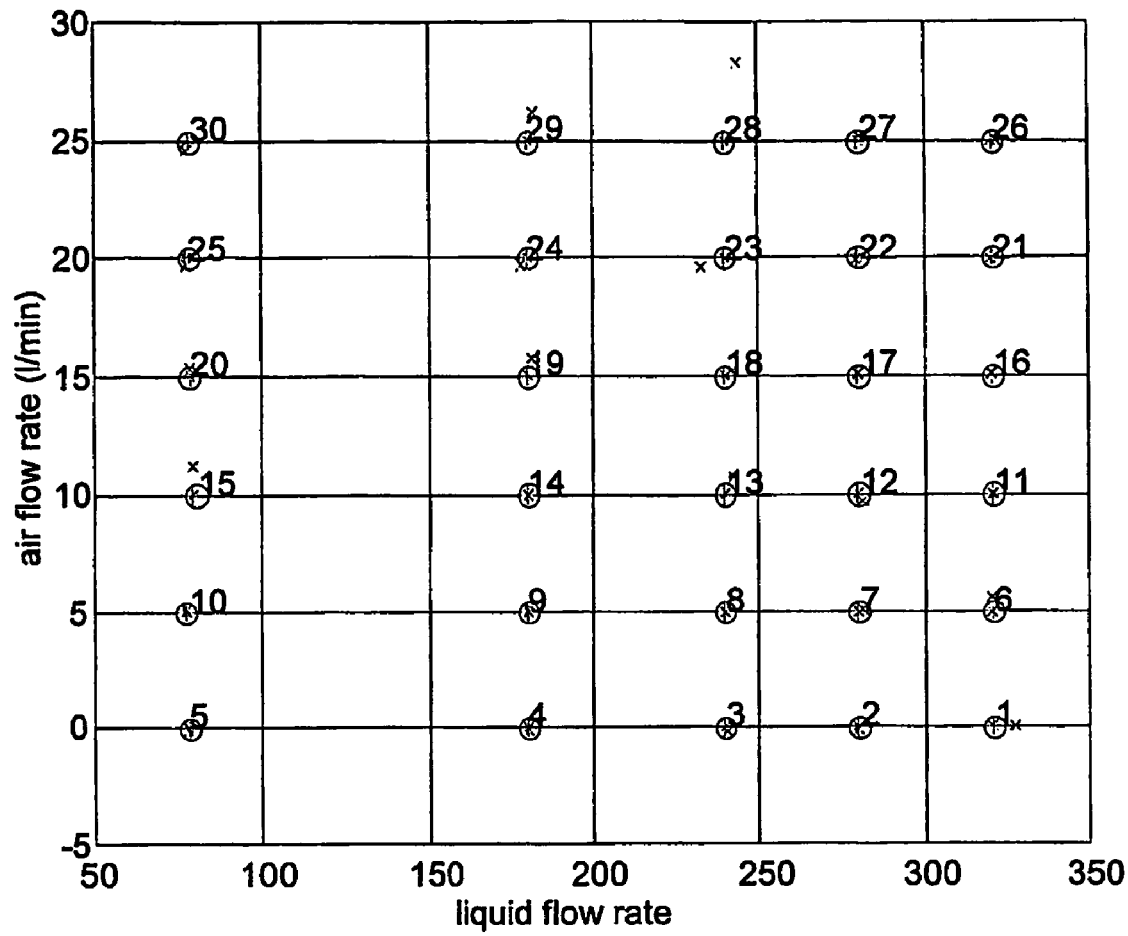
FIG. 8 represents the output from a neural network.

Two separate sets of vortex sensor signal are collected with the same conditions. The outputs of the neural network after training and testing are shown in FIG. 8 and the detailed data are given in Table 1.

As an alternative to using a trained neural network to determine the flow rates of the two components, an analytical method may be used with a more physical basis. It has been stated above that the average amplitude ($A_0$) of the vortex sensor signal for a single-phase fluid flow increases as the square of the volumetric flow rate i.e. $A_0 = a Q^2$. Hence it follows that the square root (S) of the rms amplitude should be proportional to the fluid flow rate Q. FIG. 12 shows this for the experimental data collected. The top plot is for single-phase water flow only, and is exactly linear as expected. The linear relation between S and flow rate remains approximately true even in the presence of two-phase flow, as is seen in the other plots in FIG. 12.

Figure 13:
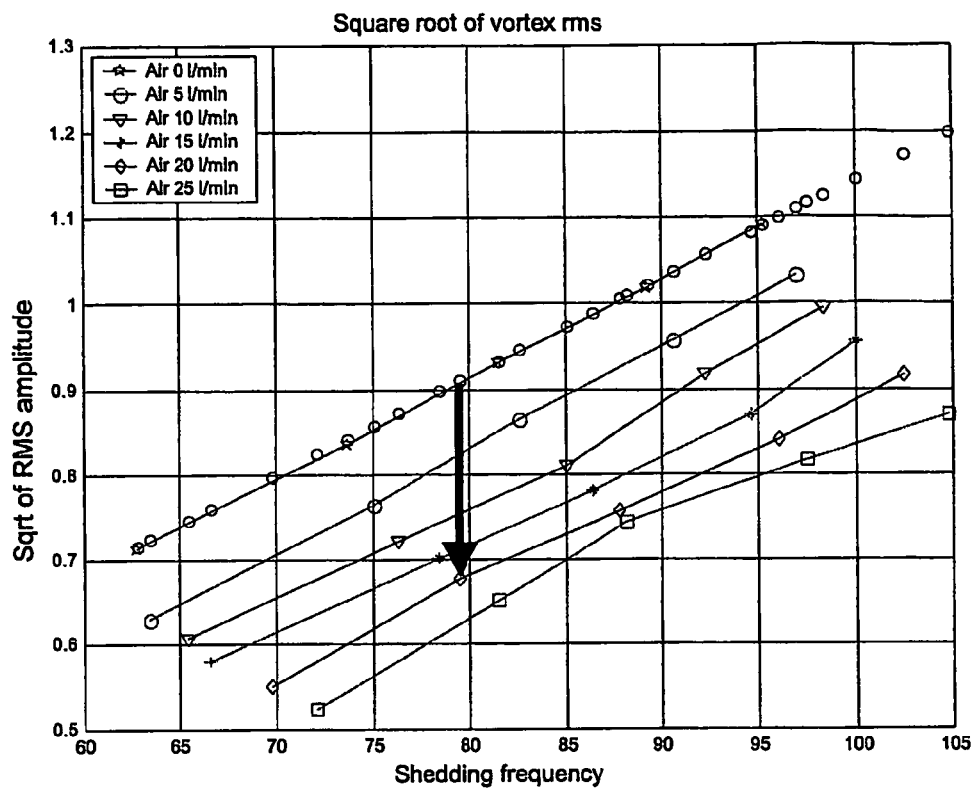
FIG. 13 shows the square root of the vortex signal amplitude plotted against shedding frequency for different two-phase flow rates. A vertical arrow is used to indicate the change in square root amplitude caused by the presence of the second phase (air).

Since shedding frequency f and the square root S of signal amplitude both vary approximately linearly with flow rate even with two-phase flow, it follows that S will vary approximately with f. This is shown in FIG. 13 for two-phase flow conditions, where each line plots S against f as the liquid flow rate L is varied, keeping the gas flow rate G constant. The different lines show the effect of differing gas flow rates G, the top line being taken with zero gas present i.e. for single phase liquid flow. The shedding frequency f is found to vary linearly with the combined volumetric flow rate (L+G) of the two phases. This again is an expected result, since the shedding frequency for single phase flow depends on fluid velocity and not on fluid physical properties, as discussed above.

FIG. 13 gives a basis for measurement of two-phase flow, since compared with the signal strength for single-phase liquid flow (top line), the signal strength S is reduced directly according to the amount of the second phase present, as indicated by the vertical black arrow for a two-phase flow combination producing a shedding frequency close to 79 Hz. The procedures for calibration of the instrument, and its use for measuring the flow rates of both components in two-phase flow are now described.

1. Calibration for 2-Phase Flow

Figure 11:
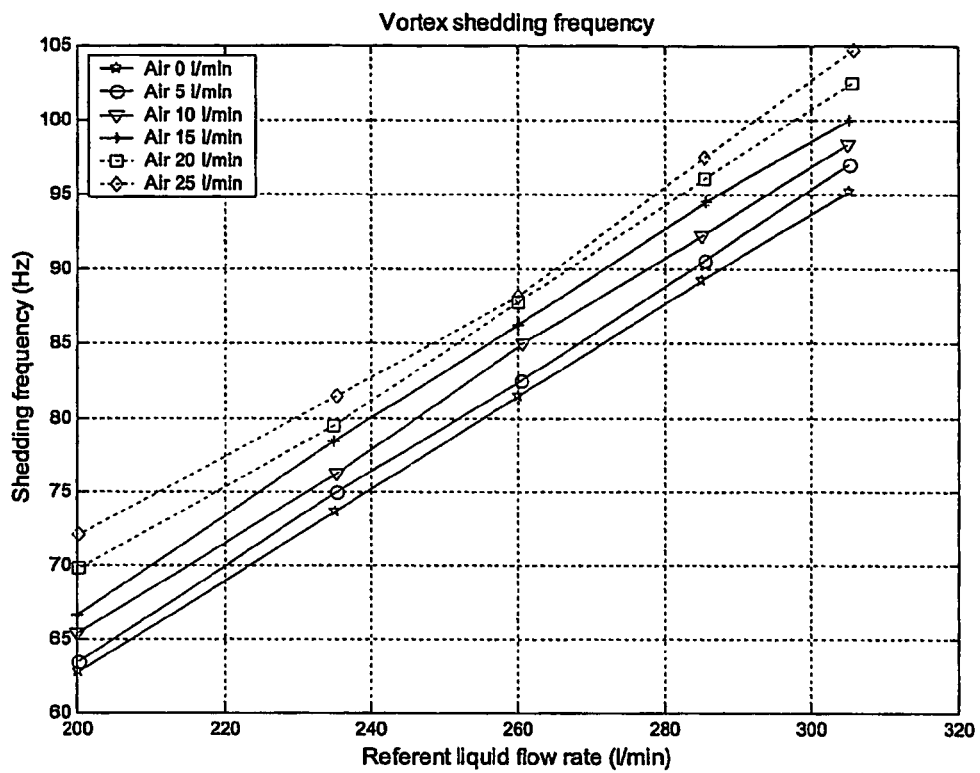
FIG. 11 shows the shedding frequency plotted against liquid flow rate for different injected air flow rates.

Calibration step 1. Given the linear relation between frequency and flow rate, we assume that the shedding frequency varies linearly with the total volumetric flow rate of the two phases i.e.

$$f = (L+G) \cdot x_1 + x_2 \qquad (6)$$

where f is the shedding frequency, L is the liquid volumetric flow rate, and G the gaseous volumetric flow rate. To determine the slope $x_1$ and intercept $x_2$, the meter is calibrated with single-phase liquid flow (G=0) from the data in the bottom plot in FIG. 11, and $x_1$ and $x_2$ determined by a least squares fit to the (f, L) data points.

Calibration step 2. We take the relation between S and L for single-phase liquid flow to be $$S_0 = y_1 + L_0 y_2 + L_0^2 y_3 \qquad (7)$$

The suffices $_0$ have been added to S and L to emphasize that this is a relation for single-phase liquid flow. Constants $y_1, y_2$, and $y_3$ are found by calibration with single-phase liquid flow using the data from the top plot in FIG. 12, and least squares fit to the ($S_0, L_0$) data points.

Calibration step 3. The effects of the presence of a second gaseous phase are taken into account as shown in FIG. 13. Each two-phase flow condition (with liquid and gas volumetric flows L & G) yields values for f and S. The shedding frequency f is used to obtain a value $L_0$ for the single-phase liquid flow which would produce the same shedding frequency f. This value $L_0$ is found from (6) with G=0 i.e.

$$L_0 = (f - x_2)/x_1 \qquad (8)$$

The corresponding value for $S_0$ is obtained from (7) i.e.

$$S_0 = y_1 + L_0 y_2 + L_0^2 y_3 \qquad (9)$$

The points (f, $S_0$) all lie on the single-phase liquid line, which is the top line in FIG. 13. They have been plotted as points (○) on the top line in FIG. 13 for each of the two-phase flow points (f, S) recorded on the plots for different air flow rates.

Calibration step 4. Whenever gaseous flow is present, the amplitude of the vortex signal is reduced, so that the actual experimental point (f, S) will lie below the single-phase water curve in FIG. 13, by an amount depending on the gaseous flow rate G. This difference ($S_0 - S$) is shown by the arrow between the upper point (f, $S_0$) and lower point (f, S) for an experimental two-phase flow point with 20 l/min of air flow.

The signal differences $S_d$ for the points are all measured $$S_d = (S_0 - S) \qquad (10)$$

(In use as a measuring instrument, $S_d$ will be used to deduce the gas flow rate G).

Calibration step 5. The $S_d$ values are fitted to the gaseous flow values G in the two-phase flow data using the quadratic relation $$G = z_2 + S_d z_3 + S_d^2 z_4 \qquad (11)$$

The experimental pairs (G, $S_d$) from the calibration flow data are used to obtain the constant parameters $z_2, z_3$, & $z_4$ by least squares fitting.

The calibration procedure above yields parameters $x_1, x_2, y_1, y_2, y_3, y_4, z_2, z_3, z_4$ that enable the meter to be used to measure the flow rates of both flow components in two-phase flow.

2. Measurement of 2-phase Flows

The calibration process in Section 4 yields parameters $x_1, x_2, y_1, y_2, y_3, y_4, z_2, z_3$, and $z_4$. Given calibrated values for the parameters, the flowmeter is then capable of measuring both flow components in two-phase flow. For a given two-phase flow causing vortex shedding frequency f and square root S of the amplitude A, the liquid flow rate L and gaseous flow rate G can be obtained as follows.

Measurement step 1. Calculate the single-phase liquid flow $L_0$ from f using $$L_0 = (f - x_2)/x_1 \qquad (8)$$

Measurement step 2. Calculate the root amplitude $S_0$ for single-phase liquid flow $L_0$ using $$S_0 = y_1 + L_0 y_2 + L_0^2 y_3 \quad (9)$$

Measurement step 3. Calculate the signal difference $S_d$ using $$S_d = (S_0 - S) \quad (10)$$

Measurement step 4. Deduce the gas flow rate G using $$G = z_2 + S_d z_3 + S_d^2 z_4 \quad (11)$$

Measurement step 5. Deduce the liquid flow rate L using $$L = L_0 - G \quad (12)$$

Figure 14:
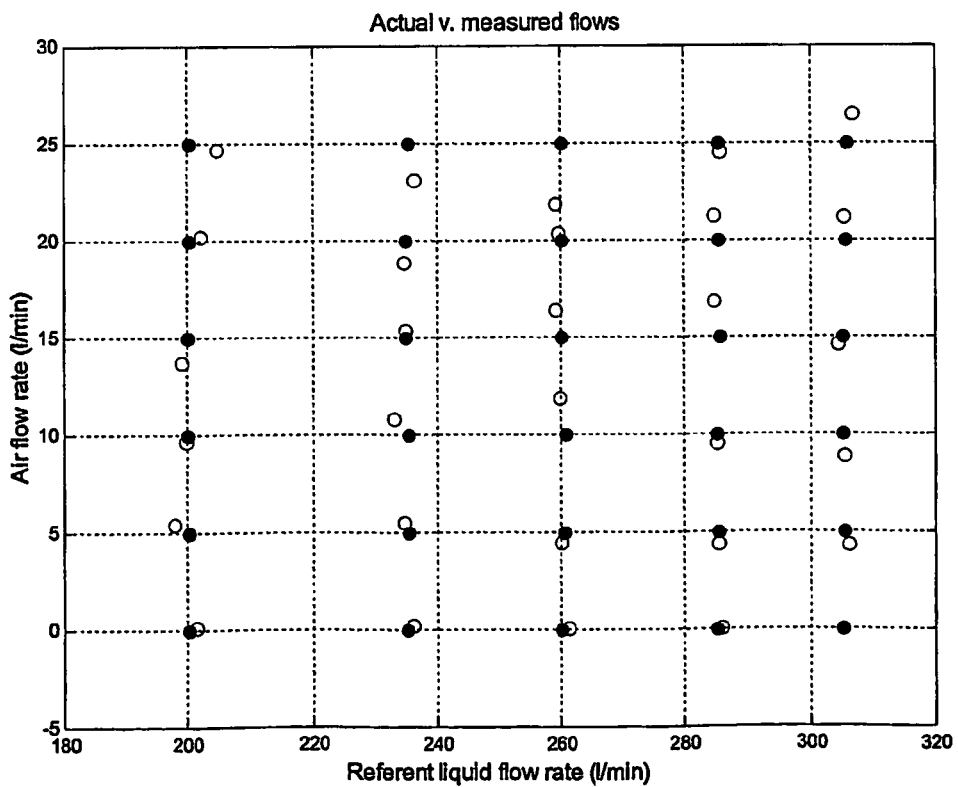
FIG. 14 is a comparison of actual flow rates (•) with flow rates (o) deduced using the calibrated parameters for the vortex meter.

Both flow rates L & G have now been found. FIG. 14 below is a plot comparing actual flow rates (•) with flow rates (○) deduced by the measurement process above using parameters found by the calibration process.

It will be appreciated that if the characteristics of a particular vortex meter deviate from the simple linear and quadratic expressions used above, that higher polynomial expansions may be used for greater accuracy. Also, to accommodate undesirable flow conditions encountered in field applications (e.g. pulsation, turbulence, and swirl), it may be necessary to allow empirical field adjustments to be made to optimise accuracy by allowing the calibrated parameter values to be varied as part of commissioning tests.

The sensor signal from a vortex meter may also be analysed to produce a very sensitive test for the presence or absence of a second fluid phase i.e. to answer the question "Is a second fluid phase present in addition to the primary fluid phase?"

This is a useful diagnostic test for single-phase flowmeters, whose accuracy is likely to be significantly reduced by the presence of a second fluid phase, as the absence of the second phase means that the user may have full confidence in the accuracy of the reading, whereas reduced accuracy must be assumed when a second phase is present.

In addition, detection of the presence of a second phase is a helpful diagnostic measurement where only one phase should be present, as the presence of the second phase may indicate an equipment fault somewhere in the system being monitored.

Figure 9:
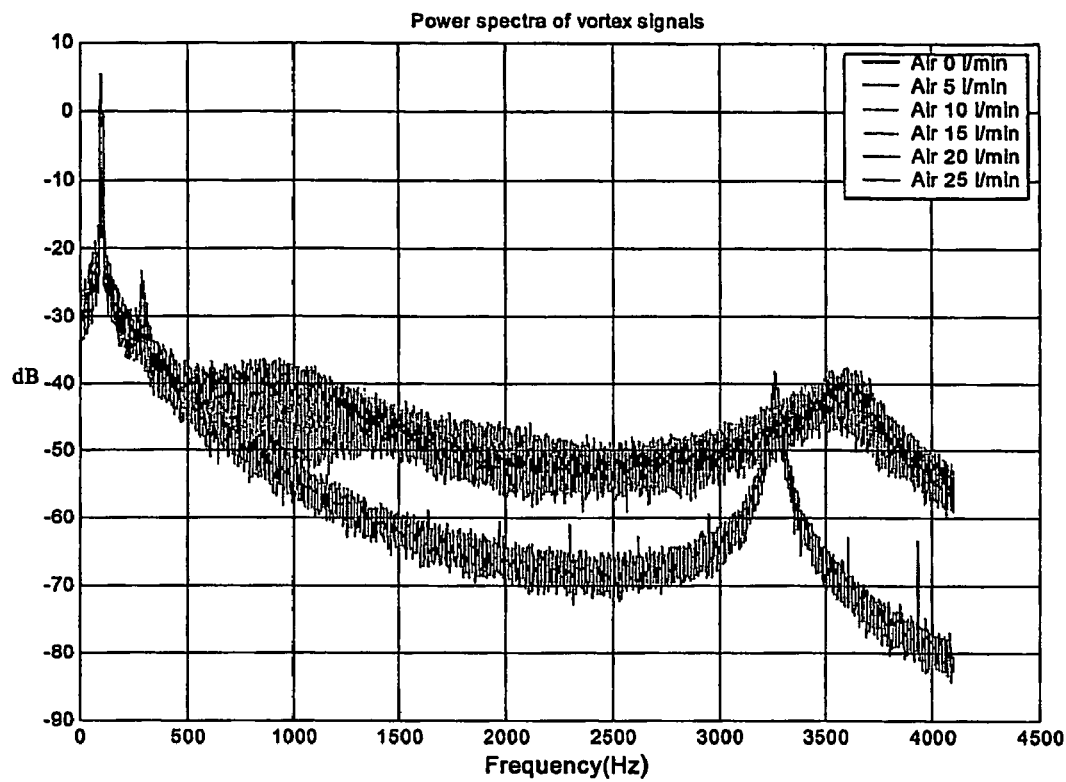
FIG. 9 shows the logarithm of the power spectrum of the primary signal from the vortex meter plotted against frequency at constant water flow rate for six different values of the second phase (air) flow rate. The presence of air increases the noise at high frequencies.

The measurement data consists of taking high frequency (e.g. up to 8 kHz) samples of the waveform of the oscillating vortex signal. If the frequency spectrum of the data is obtained by taking the Fast Fourier Transform (FFT), FIG. 9 shows plots of the frequency spectra of data taken with gas-in-water flows for differing fractions of the second phase. The plots are of the logarithm of the power spectra. It is clear that the presence of the second phase greatly increases the strength of the high frequency fluctuations in the vortex signal.

Figure 10:
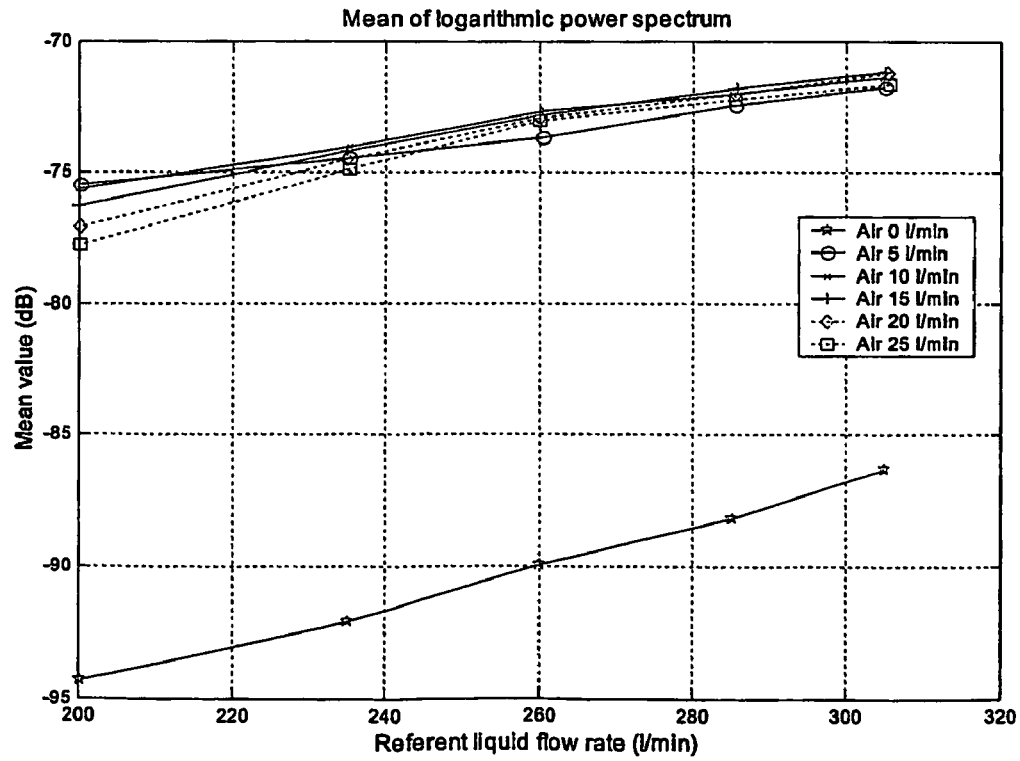
FIG. 10 shows the mean value of the logarithmic power spectrum of the vortex signal over the frequency range 0-4 kHz plotted against liquid flow rate for different injected air flow rates.

If the mean value of the logarithm of the power spectra is calculated by summing and averaging the points in each plot, FIG. 10 shows the plot of the resulting mean values from a series of two-phase flow experiments. Readings were taken as water flow rate was increased from 200 to 305 l/min in five steps, each set of readings being repeated as the air flow rate was increased in six steps of 0, 5, 10, 15, 20, and 25 l/min. Each line corresponds to a fixed air flow rate, and shows the effect of changing water flow rate.

It is seen in FIG. 10 that the mean logarithmic power values for single-phase flows plotted in the bottom line (zero air flow) lie much lower than for two-phase flows when air is present (upper curves), so that the increase in the mean value of the logarithm of the power spectrum provides a sensitive test of the presence of the second phase. Because shedding frequency is proportional to flow rate, a very similar graph is produced if the logarithm of the power spectrum is plotted against shedding frequency. An increase in the noise over a threshold value set above the level obtained from calibration data with single-phase flow at each shedding frequency then indicates the presence of a second fluid phase.

A differential pressure sensor measuring the upstream to downstream pressure drop across the vortex meter may be used as alternative signal sources to the vortex signal itself to detect the presence of a second fluid phase in the same way as described in the previous paragraph.

The present invention thus provides a method for characterising a fluid flow by using the amplitude and noise fluctuations of the sensor signal as an indication as to the status of that flow, namely whether single- or two-phase flow is present. The invention represents a clear departure from the conventional approach in flow measurement, which seeks to discard the fluctuations in the signal, whereas the present applicants have understood the importance attaching to the information contained within the noise.

TABLE 1

Measured results from the neural network
All flow rates are in l/min

| Actual water flow | Measured water flow | Error (l/min) | STD | Actual air flow | Measured air flow | Error (l/min) | STD |
|---|---|---|---|---|---|---|---|
| 320.50 | 321.624 | 1.124 | 0.5428 | 0 | 0.491 | 0.491 | 0.2584 |
| 280.00 | 280.219 | 0.219 | | 0 | −0.124 | −0.124 | |
| 240.00 | 240.366 | 0.366 | | 0 | −0.250 | −0.250 | |
| 180.00 | 180.166 | 0.166 | | 0 | −0.097 | −0.097 | |
| 77.40 | 77.423 | 0.023 | | 0 | −0.070 | −0.070 | |
| 320.50 | 320.666 | 0.166 | 1.3057 | 5 | 5.536 | 0.536 | 0.2425 |
| 280.00 | 281.439 | 1.439 | | 5 | 5.026 | 0.026 | |
| 240.00 | 239.996 | −0.004 | | 5 | 4.986 | −0.014 | |
| 180.00 | 182.510 | 2.510 | | 5 | 4.920 | −0.080 | |
| 77.00 | 77.351 | 0.351 | | 5 | 5.009 | 0.009 | |
| 320.50 | 320.650 | 0.150 | 1.3033 | 10 | 9.946 | −0.054 | 0.6778 |
| 280.00 | 281.495 | 1.495 | | 10 | 9.556 | −0.444 | |
| 240.00 | 242.188 | 2.188 | | 10 | 10.592 | 0.592 | |
| 180.00 | 180.237 | 0.237 | | 10 | 9.909 | −0.091 | |
| 79.70 | 78.520 | −1.180 | | 10 | 11.319 | 1.319 | |
| 320.50 | 320.284 | −0.216 | 1.4548 | 15 | 15.069 | 0.069 | 0.4620 |
| 280.00 | 280.064 | 0.064 | | 15 | 15.128 | 0.128 | |
| 240.00 | 241.536 | 1.536 | | 15 | 15.115 | 0.115 | |
| 180.00 | 177.177 | −2.823 | | 15 | 15.958 | 0.958 | |
| 77.80 | 78.250 | 0.450 | | 15 | 15.339 | 0.339 | |
| 320.50 | 320.593 | 0.093 | 1.8134 | 20 | 19.976 | −0.024 | 0.1610 |
| 280.00 | 278.762 | −1.238 | | 20 | 19.873 | −0.127 | |
| 240.00 | 236.788 | −3.213 | | 20 | 19.961 | −0.039 | |
| 180.00 | 182.115 | 2.115 | | 20 | 19.963 | −0.037 | |
| 77.40 | 77.726 | 0.326 | | 20 | 19.668 | −0.332 | |
| 320.50 | 322.012 | 1.512 | 2.4848 | 25 | 24.577 | −0.423 | 1.2579 |
| 280.00 | 281.328 | 1.328 | | 25 | 25.230 | 0.230 | |
| 240.00 | 234.891 | −5.109 | | 25 | 27.627 | 2.627 | |
| 180.00 | 180.815 | 0.815 | | 25 | 25.788 | 0.788 | |
| 77.99 | 77.768 | −0.222 | | 25 | 24.605 | −0.395 | |

The invention claimed is:

1. A method of monitoring or determining a flow rate of one fluid phase of a two or three phase fluid flow in a closed conduit having a vortex flowmeter through which a fluid to be monitored flows, said flowmeter having a sensor adapted to provide a signal indicative of a shedding frequency, the method comprising:

obtaining a signal from the sensor and determining from the signal a shedding frequency value related to the frequency at which vortices are shed in the vortex flowmeter, and also determining from the signal a signal amplitude-related value related to an amplitude of the signal at said shedding frequency; and using both said shedding frequency value and the amplitude-related value to determine the flow rate of the one fluid phase of the two or three phase fluid flow in the closed conduit.

2. A method according to claim 1, wherein the flow rates of two phases of the two phase fluid are simultaneously monitored using the amplitude-related-value and the shedding frequency.

3. A method according to claim 1, wherein correlations of the shedding frequency and the amplitude-related value are recorded for correlating a range of different phase relative compositions and flow rates with corresponding shedding frequency and amplitude-related values, and wherein the shedding frequency and amplitude-related values are used to determine which correlation is used to determine the flow rate of the at least one phase, or the flow rate of both phases.

4. A method according to claim 3, comprising calibrating the flowmeter by recording the range of the correlations by passing a range of different fluids with known phase compositions, at different known flow rates, through said flow meter and recording the shedding frequency and the amplitude-related values produced.

5. A method according to claim 1, comprising using a linear relationship between the shedding frequency and a total volume flow rate of all fluid phases to determine a total flow rate, and using said amplitude-related value to determine the relative amount of the different phases in the fluid.

6. A method according to claim 1, wherein the flow rate of the one fluid phase is determined individually from a flow rate of a second fluid phase of the two or three phase fluid flow in the closed conduit.

7. Apparatus for monitoring or determining a flow rate of at least one phase of a two or three phase fluid flow adapted to operate on a signal from a sensor of a vortex flowmeter to derive a shedding frequency value related to a shedding frequency of vortices in the flowmeter and also to derive an amplitude-related value related to an amplitude of the signal at the shedding frequency, and adapted to use the shedding frequency value and the amplitude-related value to determine the flow rate, said apparatus calibrated with correlation data correlation, for a plurality of different fluid phase compositions, a plurality of different total volume flow rates with corresponding shedding frequency and amplitude-related values.

8. A method of calibrating a vortex flowmeter to enable a sensor of the flowmeter to provide a signal that is indicative of either a presence of two phase fluid flow, or a flow rate of one phase of the two phase flow, the method comprising:
   determining, and recording, for the flowmeter, for a range of total volume flow rates, at a range of different amounts of each phase of the two phase fluid flow, a shedding frequency value and associated amplitude value of the signal, and
   calibrating the vortex flowmeter using the determined shedding frequency values and associated amplitude values.

9. A method of detecting two-phase fluid flow in a closed conduit which has a vortex flowmeter though which the fluid flows, the method comprising obtaining from a sensor signal both a shedding frequency value related to the shedding frequency of vortices shed by the flowmeter, and also an amplitude value related to an amplitude of the signal, and using a significant change in the amplitude value to detect a change between the fluid having one phase and the fluid having two phases.

10. A method of monitoring a multiple phase fluid flow in a closed conduit including a vortex flowmeter through which the fluid to be monitored flows, the flowmeter operable to generate a signal indicative of a vortex shedding frequency associated with the fluid flow, the method comprising:
   measuring the sensor signal, determining signal components relating to both the shedding frequency of said signal and an amplitude of said signal at the shedding frequency, and analysing the shedding frequency and amplitude signal components of said signal to monitor a characteristic of the multiple phase fluid flow.

11. A method of monitoring according to claim 10 for detecting two-phase fluid flow comprising analyzing the shedding frequency and the amplitude signal components to detect the presence or an absence of the two-phase fluid flow.

12. method of monitoring according to claim 11 comprising taking samples of a waveform of an oscillating vortex shedding frequency signal for a single phase fluid flow, obtaining a first frequency spectrum by taking the first Fast Fourier Transform, calculating a first logarithm of the values of the first frequency spectrum, and calculating a first mean value of the first logarithm of the values of the first frequency spectrum to provide a first datum for single-phase fluid flow, taking subsequent samples of the waveform of the oscillating vortex shedding frequency signal from the two-phase fluid flow, obtaining a second frequency spectrum by taking the Fast Fourier Transform, calculating a second logarithm of the values of the second frequency spectrum, and calculating a second mean value of the second logarithmic of the values of the second frequency spectrum to provide a second datum for the two-phase fluid flow and comparing the second mean value of the second logarithm against the first datum for single phase flow to detect the presence or absence of the two-phase fluid flow.

13. A method of monitoring according to claim 10 comprising analyzing the said shedding frequency and the amplitude signal components to determine a volumetric flow rate of at least one phase of the fluid flow.

14. A method according to claim 10 for a liquid gas two phase fluid regime further comprising the steps of calibrating the flowmeter using a first reference flowmeter to measure a liquid flow rate and a second reference flow meter to measure the gas flow rate thereby to determine a relationship between the signal amplitude components, the shedding frequency of vortices generated within the vortex flowmeter, the liquid flow rates of the gas flow rate.

15. A method according to claim 14, wherein the calibrating includes conducting a series of tests to provide a performance data over a range of flow rates with a single phase flow and the two-phase flow.

16. A method according to claim 15, wherein at least a step is performed from:
   (i) a multi layer neural network is employed as a method of handling the said performance data to provide measured values for primary phase flow and a secondary phase flow;
   (ii) an analytical method is employed to handle the performance data to provide measured values of a primary phase flow and a secondary phase flow;
   (iii) the calibrating is conducted with the two-phase flow on the basis of liquid-in-gas phases;
   (iv) the calibrating is conducted with the two-phase flow on the basis of gas-in-liquid phases.

17. A method according to claim 14, wherein a liquid is flowing at a constant rate and a gas is introduced at a point, thereby causing an increase in a mean velocity of flow, the increase in the mean velocity of the flow being itself indicative of the presence of a secondary fluid phase.

18. A method according to claim 10, wherein an increase in the vortex shedding frequency occasioned by virtue of an increase in a mean velocity of flow is accompanied by a decrease in the amplitude of the shedding frequency signal in the sensor signal.

19. A method according to claim 17, wherein a decrease in the amplitude of the sensor signal is used as a determinant as to a presence of the secondary fluid phase.

20. A method according to claim 10, wherein a relative magnitude of two phases is determined by the analysis and manipulation of the sensor signal from the vortex flowmeter.

21. A method of monitoring according to claim 10 for detecting two-phase fluid flow in the fluid flow in the closed conduit including the disposition of the vortex flowmeter through which the fluid to be detected flows, generating the signal indicative of at least one characteristic of the fluid flow, wherein measuring pressure fluctuations from an upstream to a downstream differential pressure across the vortex flowmeter, to generate a fluctuation signal, taking samples of the waveform of the differential pressure signal or pressure signal and retaining the fluctuations associated therewith for a single phase fluid flow, obtaining a frequency spectrum by taking the Fast Fourier Transform of the signal, calculating the logarithm of the spectral values, and calculating the mean value of the logarithmic spectral values to provide a datum for single phase fluid flow, taking subsequent samples of the waveform of the differential pressure or pressure signal and retaining the fluctuations associated therewith from the two-phase fluid flow, obtaining a frequency spectrum by taking a Fast Fourier Transform, calculating a logarithm of the spectral values, and calculating a mean value of logarithmic spectral values, and comparing a logarithmic mean value against the datum for single phase fluid flow to detect a presence or an absence of the two-phase fluid flow.

* * * * *